(12) United States Patent
Demjanenko

(10) Patent No.: US 10,543,349 B2
(45) Date of Patent: Jan. 28, 2020

(54) DEVICE FOR PIERCING AN ORGANIC TISSUE AND ACTUATION MODULE

(75) Inventor: Dmitrij Demjanenko, Berlin (DE)

(73) Assignee: MT. DERM GMBH, Berlin (DE)

( * ) Notice: Subject to any disclaimer, the term of this patent is extended or adjusted under 35 U.S.C. 154(b) by 316 days.

(21) Appl. No.: 13/450,253

(22) Filed: Apr. 18, 2012

(65) Prior Publication Data
US 2013/0123825 A1  May 16, 2013

(30) Foreign Application Priority Data
Nov. 16, 2011 (EP) .................................. 11 189 360

(51) Int. Cl.
*A61M 37/00* (2006.01)

(52) U.S. Cl.
CPC .............................. *A61M 37/0076* (2013.01)

(58) Field of Classification Search
CPC .......... A01K 11/005; A61M 2205/106; A61M 37/0076; A61M 5/3287; D05B 69/00; D05B 69/08; D05B 69/10
USPC ................... 606/185, 167, 182, 181
See application file for complete search history.

(56) References Cited

U.S. PATENT DOCUMENTS

| | | | | |
|---|---|---|---|---|
| 464,801 A * | 12/1891 | O'Reilly | ........... | A61M 37/0084 81/9.22 |
| 4,031,783 A * | 6/1977 | Paul | .................. | A61M 37/0076 81/9.22 |
| 4,203,446 A * | 5/1980 | Hofert | .............. | A61B 5/150022 173/114 |
| 5,106,364 A * | 4/1992 | Hayafuji | .......... | A61B 17/32002 30/208 |
| 5,741,288 A * | 4/1998 | Rife | .............................. | 606/181 |
| 6,033,421 A * | 3/2000 | Theiss | ............... | A61M 37/0076 606/186 |
| 6,065,371 A | 5/2000 | Yacowitz | | |
| 7,374,544 B2 * | 5/2008 | Freeman et al. | ............... | 600/583 |
| 2005/0010236 A1 * | 1/2005 | Frister | ........................... | 606/116 |

(Continued)

FOREIGN PATENT DOCUMENTS

EP        1958659 A1    8/2008

OTHER PUBLICATIONS

Extended European Search Report, directed to European Patent No. 11189360, dated Apr. 12, 2012, 7 pages.

*Primary Examiner* — Sarah A Simpson
(74) *Attorney, Agent, or Firm* — Leason Ellis LLP

(57) ABSTRACT

The invention relates to a device for piercing an organic tissue, and more particularly to piercing human or animal skin. The device includes a housing, a piercing unit, which is accommodated in the housing, and an actuator device which is arranged and configured in the housing to generate an actuating force in such a way that an actuator component surrounded by the actuator device and functionally connected to the piercing unit, performs an oscillating actuating movement in the housing which is coupled to the piercing unit. The actuating device is designed with a counter component allocated to the actuating component which at least partially compensates for vibrations caused in the housing by the oscillating actuating movement of the actuating component; the counter component oscillates and is moved contrary to the actuating component. The invention also relates to an actuation module for a device for piercing an organic tissue.

18 Claims, 8 Drawing Sheets

(56) References Cited

U.S. PATENT DOCUMENTS

Figure 1A:
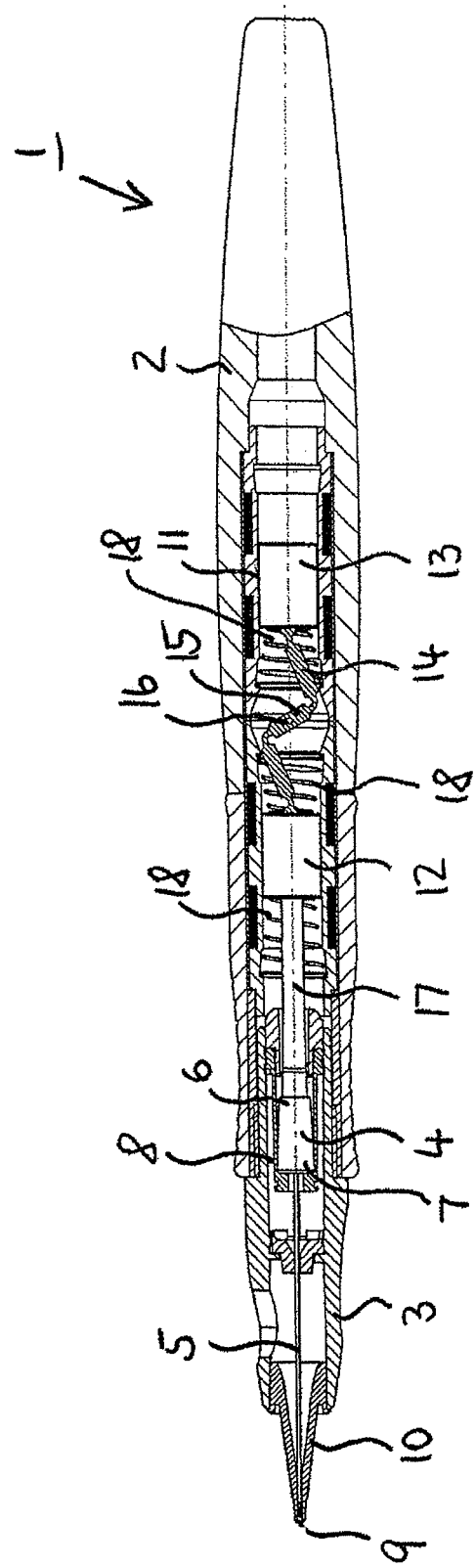
Figure 1B:
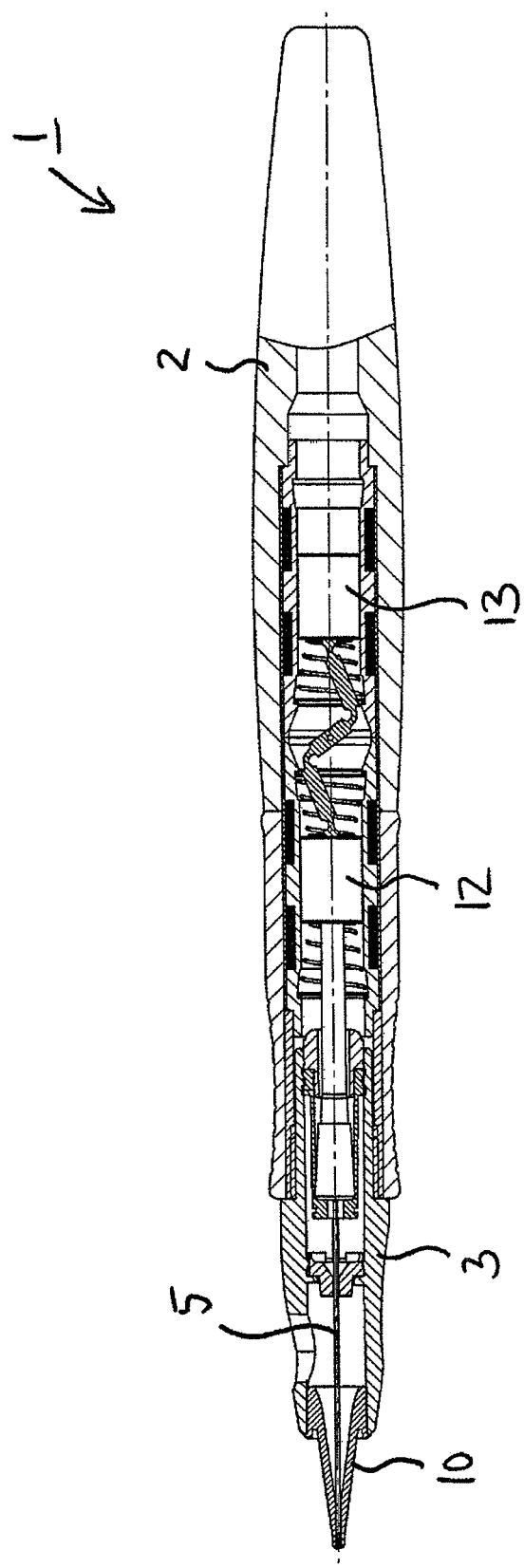
Figure 1C:
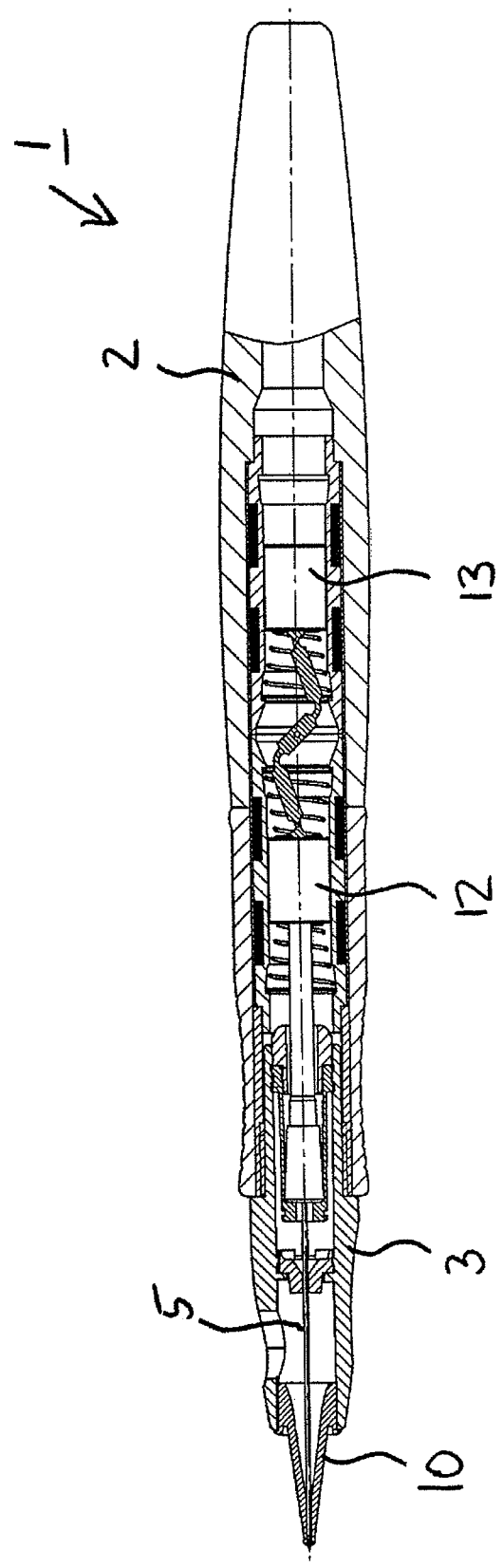
Figure 1D:
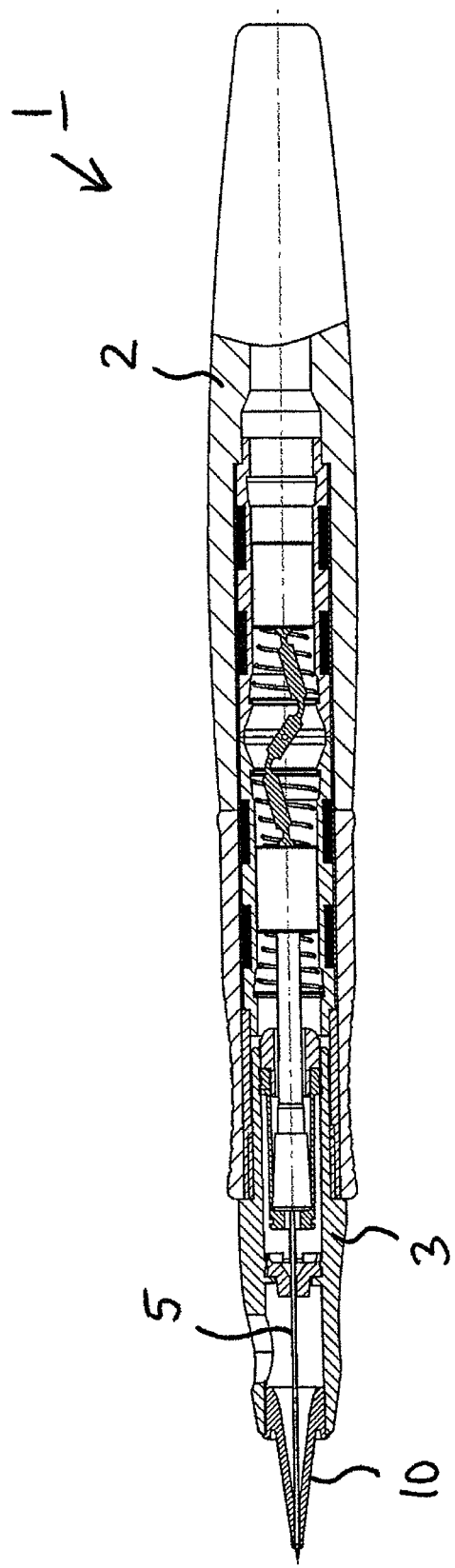

| | | | | |
|---|---|---|---|---|
| 2005/0277973 A1* | 12/2005 | Huang | ............... | A61M 37/0076 |
| | | | | 606/185 |
| 2007/0100364 A1* | 5/2007 | Sansom | ........................ | 606/181 |
| 2008/0306502 A1 | 12/2008 | Lisec et al. | | |
| 2010/0106058 A1* | 4/2010 | Douglas | ............. | A61B 5/15196 |
| | | | | 600/583 |
| 2012/0158029 A1* | 6/2012 | Underwood | ..... | A61B 17/32002 |
| | | | | 606/171 |

* cited by examiner

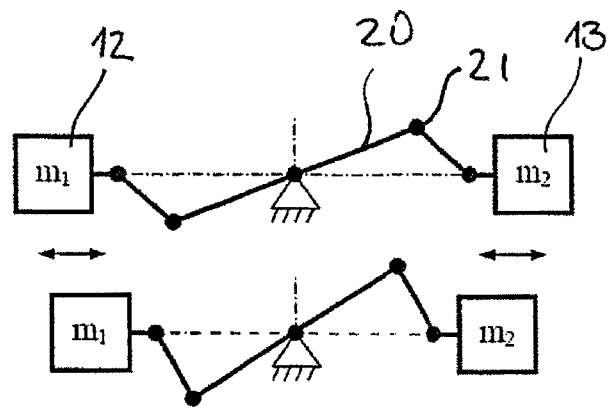
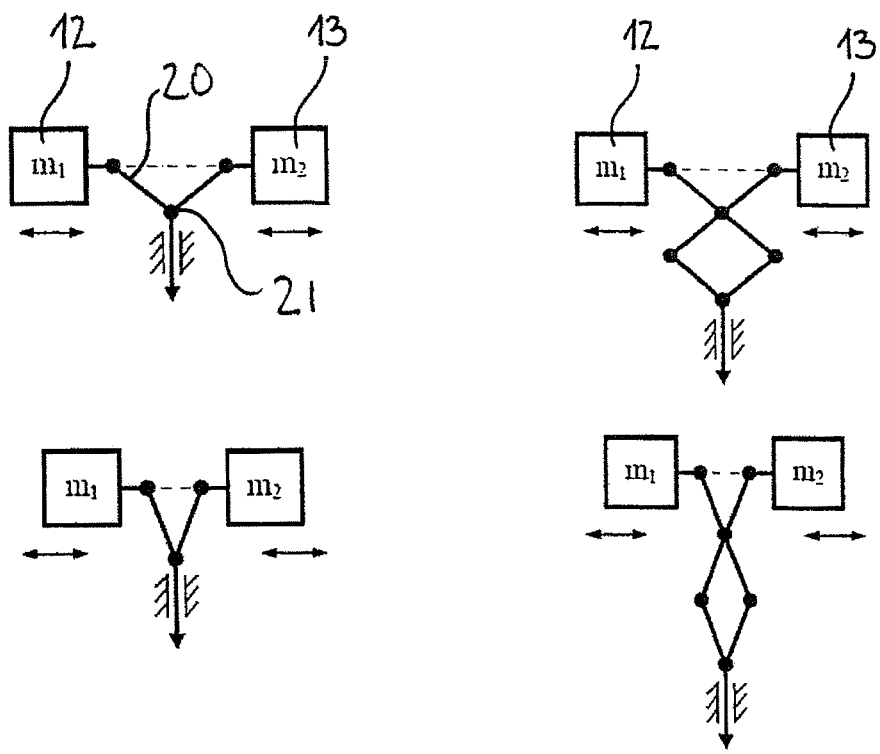
fig. 2
fig. 3

DEVICE FOR PIERCING AN ORGANIC TISSUE AND ACTUATION MODULE

BACKGROUND TO THE INVENTION

Field of the Invention

The invention relates to a device for piercing an organic tissue, more particularly human or animal skin, and an actuation module.

Discussion of the Related Art

Devices of this type are used in order to provide organic tissue, more particularly human or animal skin, with one or more tissue openings. If necessary a fluid active substance can then be introduced into the tissue through the tissue openings. Such piercing devices are used, for example, for introducing a dye in connection with tattooing or creating permanent make-up. But the introduction of other active substances such as medicinal or cosmetic substances can also be envisaged in conjunction with this.

Normally, in known piercing devices, a piercing unit, which is provided with one or more needles, is held on a housing and moved to and fro in an oscillating manner with the aid of a actuating device so that repeated piercing of the organic tissue takes place. The oscillating movement of elements of the actuation device and finally the piercing unit causes the device, which is designed as a hand-held device, to vibrate. The user must then absorb these vibrations with the hand with which he or she is holding the piercing device. The vibration of the device is perceived as unpleasant by the user.

SUMMARY OF THE INVENTION

The aim of the invention is to provide a device for piercing an organic tissue as well as an actuation module for such a device, which exhibit improved user comfort, more particularly in that vibrations by the device or elements thereof are reduced or suppressed entirely.

In accordance with the invention this aim is achieved by a device for piercing an organic tissue, more particularly human or animal skin, in accordance with independent claim 1. In addition an actuation module is created for a device for piercing an organic tissue, more particularly human or animal skin, in accordance with independent claim 11. Advantageous embodiments of the invention form the subject matter of the dependent sub-claims.

The invention covers the concept of a device for piercing an organic tissue, more particularly human or animal skin, with a housing, a piercing unit, which is accommodated in the housing, and an actuator device which is arranged and configured in the housing to generate an actuating force in such a way that an actuator component is part of the actuator device and functionally connected to the piercing unit, performs an oscillating actuating movement in the housing which is coupled to the piercing unit, whereby the actuating device is designed with a counter component to the actuating component which at least partially compensates vibrations caused in the housing by the oscillating actuating movement of the actuating component, in that during the oscillating actuating movement of the actuating component, the counter component oscillates and is moved contrary to the actuating component.

In accordance with a further aspect of the invention an actuation module for a device for piercing an organic tissue, more particularly human or animal skin, with the following features is created: a module housing and an actuating device, which is arranged and configured in the module housing to connect to a needle module and to generate an actuating force, so that an actuator component is part of the actuator device and functionally connected to the piercing unit, performs an oscillating actuating movement in the housing which is coupled to the piercing unit whereby the actuating device is designed with a counter component to the actuating component which at least partially compensates vibrations caused in the housing by the oscillating actuating movement of the actuating component, in that during the oscillating actuating movement of the actuating component, the counter component oscillates and is moved contrary to the actuating component.

With the invention a device for piercing an organic tissue as well as an actuation module for such a device are created, in the case of which vibrations of the housing and/or other elements of the device are reduced or entirely prevented, in that the actuating device is designed with an additional component, namely a counter component or compensation component, which also oscillates with the oscillating actuating movement, but is moved in the opposite direction. In this way vibration forces or impulses, resulting from the oscillating actuating movement, which can also be described as a repetitive movement, are compensated either entirely or partially by counter forces/impulses provided by the additional counter component. In this way a reduction in the vibration of the device is achieved.

The housing of the device can be designed in one or multiple parts. In the case of a multiple-part embodiment the device can be designed with several separable housing parts each of which can form one or more functional modules with components accommodated therein, more particularly an actuation module with the actuating device and a detachably connected piercing or needle module which holds the piercing unit. The modules are preferably detachably connected to each other, for example by means of a plug and/or screw-type connection. In one form of embodiment the piercing or needle module can be designed as a disposable module, which can be provided, for example, as a consumable article in the form of a sterilised module for single use. Alternatively, or additionally, other functional modules can be coupled to the housing, for example a reservoir or a tank with a fluid active substance.

The piercing unit can be formed with a single needle and/or a needle plate, on the outward facing surface of which several needle tips are arranged, as for example in the form of micro-needle tips. The coupling of the piercing unit to the actuating component is either direct or mediated by means of one or more coupling elements.

A preferred further development of the invention envisages that the oscillating actuating movement is an axial actuating movement. Here the actuating component is moved back and forth in the longitudinal direction of the housing. In connection with this it can also be envisaged that the counter component is also moved axially during the oscillating movement in the opposite direction.

In an expedient embodiment of the invention it can be envisaged that the actuating component and the counter component or compensation component are arranged in a kinematic chain. Preferably the actuating component and the counter component are connected by means of one or more intermediately arranged chain elements. The kinematic chain brings about a kinematic coupling of the actuating component and counter component. Moving the actuating component then necessarily also leads to movement of the counter component. The kinematic coupling is configured to bring about an opposing movement of the actuating component and counter component. The kinematic chain is preferably designed as an open chain. In one embodiment the component and counter component are connected by means of an odd number of chain elements connected in an articulated manner, of which the middle chain element can rotated about a point of rotation.

An advantageous form of embodiment of the invention envisages that the mass of the actuating component is essentially equal to the mass of the counter component. In this form of embodiment the actuating component and counter component are preferable displaced with the same vibration amplitude during each oscillating movement. In an alternative embodiment the mass of the counter component can be greater than the mass of the actuating component, for example for at least partially compensating for the mass of the piercing unit, which connects to the actuating component and/or another component coupled to the actuating component which is also moved during the oscillating movement of the actuating component. Here it can be envisaged that the actuating component and the counter component perform a contrary movement with different vibration amplitudes.

Preferably a further development of the invention envisages that an elastic spring element is assigned to the actuating component in the oscillating actuating movement at least in terms of a forward movement or at least in terms of a backward movement. The elastic spring element can for example designed as a pressure or tension spring element. The sprung element converts the kinetic energy of the assigned oscillating component, i.e. of the actuating component or the counter component, into potential energy, for example into mechanical tensioning of the pressure spring, which can then again be converted into kinetic energy of the assigned component, whereby, however, certain losses occur.

In an advantageous embodiment of the invention it can be envisaged that an elastic spring element is assigned to the counter component in opposite direction to the oscillating actuating movement at least in terms of a forward movement or at least in terms of a backward movement. The elastic spring element can for example be designed as a pressure or tension spring element. The above explanations relating to the spring element assigned to the actuating component apply accordingly.

A further development of the invention can envisaged that the counter component is designed as a passive component, which is passively moved during the oscillating actuating movement of the actuating component. In this embodiment the counter component is passively moved by the actuating component.

A preferred further development of the invention envisages that the counter component is designed as an active component which during the oscillating actuating movement of the actuating component is actuated by means of a component actuating device assigned to the counter component and thus actively moved. In this form of embodiment the counter component is actuated itself, for example, by way of an electromagnetic actuator, whereby a mechanically contact-free actuating device is preferred.

In an expedient embodiment of the intention it can be envisaged that the actuating device is configured to actuate the actuating component and/or the counter component in a mechanically contact-free manner. In this embodiment the actuating component and/or the counter component are, for example, moved in a mechanically contact-free manner within an electromagnetic field.

In connection with the actuation module for the device for piercing an organic tissue the statements made in connection with the further developments of the device apply accordingly.

The actuating device is preferably configured to provide a linear oscillating actuating force which can be directly coupled to the piercing unit, i.e. free of a kinematic movement conversion as is necessary, for example, in actuating devices which produce a rotary drive movement by means of a motor. Irrespective of the provision of the counter component, which can then also optionally be omitted, a device for piercing organic tissue, more particularly human or animal skin, is created with a housing, a piercing unit which is accommodated in the housing and an actuating device, which is arranged and configured in the housing to generate am oscillating, linearly acting actuating force, so that an actuating component which is part of the actuating device and is functionally coupled to the piercing unit, performs an oscillating actuating movement in the housing which is coupled to the piercing unit. The oscillating, linearly acting actuating force, is preferably aligned axially to the housing axis. Here too, in one embodiment the actuating device can be designed with a counter component assigned to the actuating component which at least partially compensates for the vibrations caused in the housing by the oscillating actuating movement of the actuating component in that during the oscillating actuating movement of the actuating component the counter component oscillates in the housing and is moved contrary to the actuating component.

DETAILED DESCRIPTION OF THE
PREFERRED EMBODIMENTS

Figure 4:
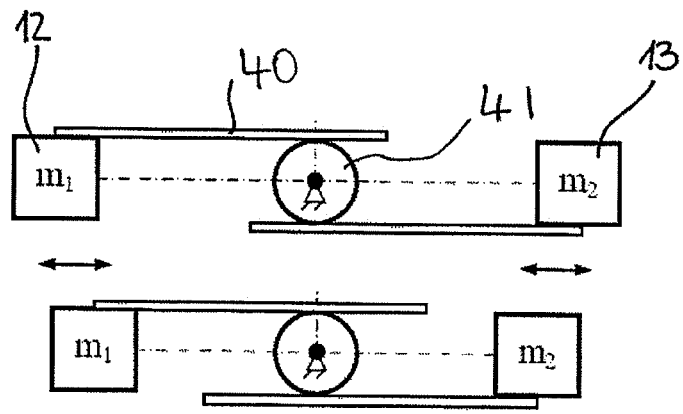
Figure 5:
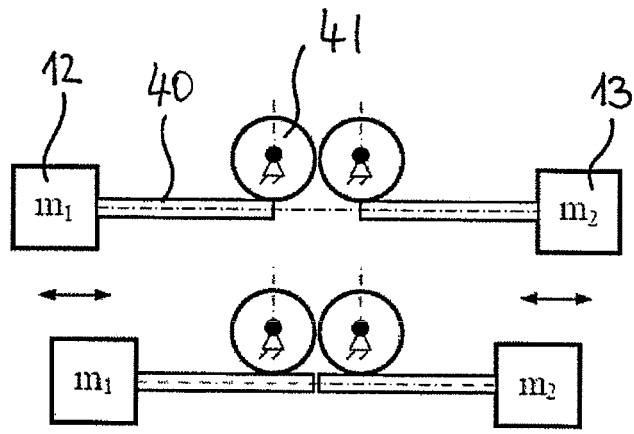
Figure 6:
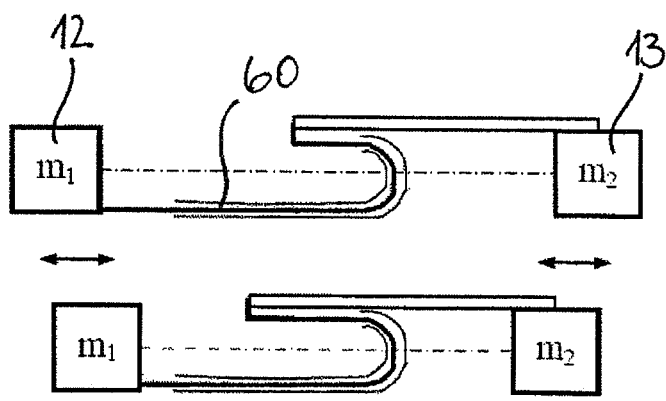
Figure 7:
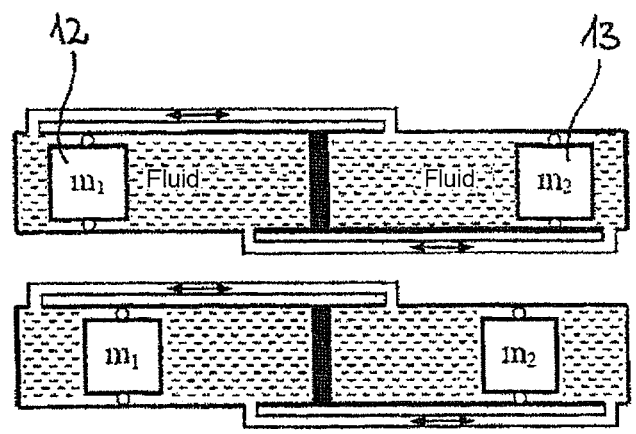
Figure 8:
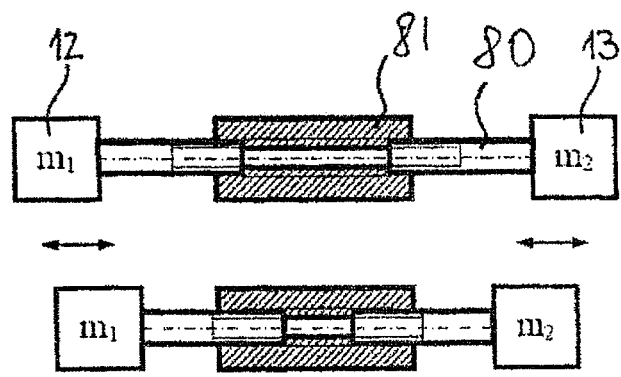
Figure 9:
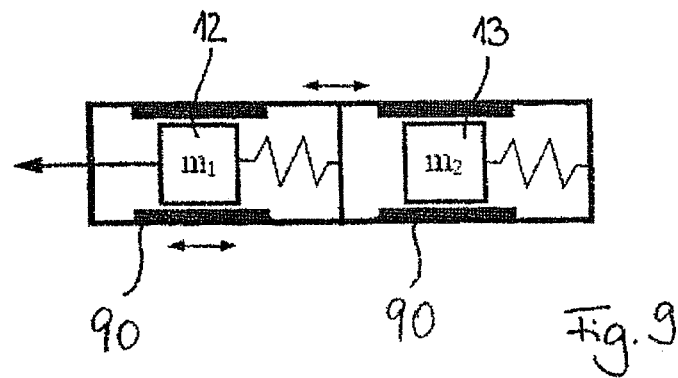

The invention will be described in more detail below by way of preferred examples of embodiment with reference to figures of a drawing. Here FIGS. 1a-1e show a schematic view in cross-section of a hand-held device for piercing an organic tissue, FIG. 2 shows a schematic view of a mechanical coupling of an actuating component and a counter component, FIG. 3 shows a schematic view of a further mechanical coupling of an actuating component and a counter component, FIG. 4 shows a schematic view of a mechanical coupling by means of racks and a cogwheel of an actuating component and a counter component, FIG. 5 shows a schematic view of a mechanical coupling of a component and a counter part by means of racks and several cogwheels, FIG. 6 shows a schematic view of a coupling of an actuating component and a counter component by means of a cable, FIG. 7 shows a schematic view of a fluidic coupling of an actuating component and a counter component, FIG. 8 shows a schematic view of a mechanical coupling of an actuating component and a counter component by means of a threaded screw and FIG. 9 shows a schematic view of a form of embodiment for a contrary movement of an actuating component and counter component using coils FIGS. 1a to 1e show a hand-held device 1 for piercing an organic tissue, more particularly human or animal skin, in cross-section. The device 1 has an actuation module 2 as well as a needle module 3 detachably connected thereto. In the needle module 3 a piercing unit 4 is arranged which in the shown form of embodiment is formed with one needle 5. At the back the needle 5 is held on a needle carrier 6, which in turn is placed with a front section 7 in an elastic membrane 8. In operation the needle is extended and retracted through an opening 9 of a needle nozzle 10 in an oscillating manner, so that an organic tissue can be pierced. During this the elastic membrane 8, which is in a U or pot shape, is stretched on extension of the needle 5 and in this way provides an optionally supporting return force for the return movement (retraction) of the needle carrier 6 and the needle 8. For this the elastic membrane 8 is fixed in the rear section of the needle module 3.

Arranged in the actuation module 2 is an actuating device 11 which in the shown form of embodiment is designed with an electrodynamic actuator which directly provides a linear actuating movement which is then coupled to the piercing unit 4. In contrast to a conventional DC motor the linear actuator provides a linearly repeating actuating force. To this extent it is a direct drive. To operate the piercing unit 4 no kinematic conversion of the rotating movement of the DC motor into a linear movement is necessary.

Assigned to the actuating device 11 are an actuating component 12 as well as a counter component 13, which via intermediate elements 14—three intermediate elements in the shown form of embodiment—connects a kinematic chain to the actuating component 12. A central intermediate element 15 is rotatably borne about a rotation point 16. The actuating component 12 and counter component 13 are moved in an axial oscillating manner in the shown example of embodiment. In the shown form of embodiment the actuating component 12 connects to a plunger 17 which is turn is connected to the needle carrier 6.

Figure 1E:
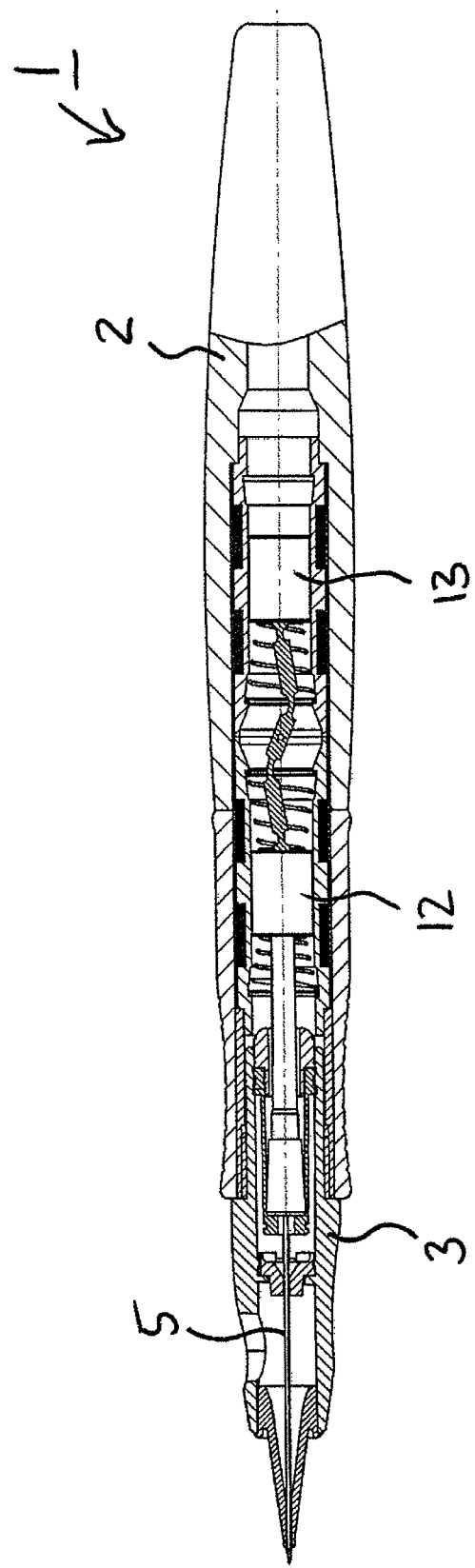

The view in FIGS. 1a to 1e show the kinematic chain in different positions so that the needle 5 in the view in FIG. 1a is completely retracted into the needle module 3 and completely extended in the view in FIG. 1e.

The intermediate elements 14 bring about kinematic coupling of the actuating component 12, which in turn connects to the needle carrier 6 and the counter component 13, so that the counter component 13 is always axially moved when the actuating component 12 is actuated by means of the actuating device 11. The movements of the actuating component 12 on the one hand and the counter component 13 on the other hand are exactly opposite to each other. This results in at least partial equalisation of the oscillations or vibrations which are produced during the oscillating movement of the actuating component 12 and transmitted to the housing of the device 1.

In accordance with the view in FIG. 1 the central intermediate element 15 is rotatably borne in the rotation point 16. The actuating component 12 as well as the counter component 13 are moved against elastic spring elements 18 during each oscillating movement. In this way linear oscillating actuation is produced.

FIGS. 2 to 9 show various forms of embodiments with the actuating component 12 (m1) and the counter component 13 (m2).

FIG. 2 shows a schematic view of a mechanical coupling of the actuating component 12 and the counter component 13. The coupling between the actuating component 12 and the counter component 13 takes place via levers 20 which are connected to each other by means of joints 21. The joints 21 can be designed as sliding bearings or as elastic connections, for example, by means of silicone or another plastic or by means of spring steel.

FIG. 3 shows a schematic view of a further mechanical coupling of the actuating component 12 and the counter component 13. The coupling between the actuating component 12 and the counter component 13 is again via levers 20 which are connected to each other by means of joints 21.

FIG. 4 shows a schematic view of a mechanical coupling by way of racks and a cogwheel of the actuating component 12 and the counter component 13. The components are coupled by means of racks 40 and a cogwheel 41.

FIG. 5 shows a schematic view of a mechanical coupling of the actuating component 12 and the counter component 13 by means of racks 40 and several cogwheels 41.

FIG. 6 shows a schematic view of a coupling of the actuating component 12 and the counter component 13 by means of cables 60.

FIG. 7 shows a schematic view of a fluidic coupling of the actuating component 12 and the counter component 13. Here a fluidic coupling is envisaged in which the moving components displace a fluid which in turn brings about the movement of the other components. The fluid is only slightly compressible or non-compressible.

FIG. 8 shows a schematic view of a mechanical coupling of the actuating component 12 and the counter component 13 by means of a threaded screw 80 with a large thread pitch so that the liner movement of the actuating component 12 is converted into a rotating movement of a sleeve 81, which in turn results in a linear movement of the counter component 13.

FIG. 9 shows a schematic view of a form of embodiment of opposing movement of the actuating component 12 and the counter component 13 using coils 90. The actuating component 12 and the counter component 13 are sprung and are each actuated by means of the allocated coil 90. The opposing movement of the actuating component 12 and counter component 13 is actively brought about here without kinematic coupling of the components.

The features of the invention disclosed in the above description, the claims and in the drawing can be of relevance both individually as well as in any combination for implementing the invention in its various forms of embodiment.

What is claimed is:

1. A device for piercing an organic tissue comprising:
a housing;
a piercing unit, which is accommodated in the housing;
a vibration drive selected from the following group: a parallel vibration motor, a Lorentz force-driven linear actuator with movable coil or movable rotors, a Piezo actuator, an ultrasonic actuator, a pneumatic vibration actuator and an electrodynamic linear actuator; and
an actuating device arranged within the housing and having an actuating component and a counter component, the actuating device being driven directly by the vibration drive to produce a linear oscillating actuating movement of at least the actuating component free of any conversion of a rotary drive movement,
wherein the actuating component is mechanically coupled to the piercing unit and the counter component is assigned to the actuating component so as to move in a direction contrary to the linear oscillating actuating movement of the actuating component,
whereby actuating of the vibration drive drives the actuating device to cause a linear oscillating actuating movement of the piercing unit while the counter component at least partially compensates for any vibration in the housing caused by movement of the actuating component.

2. The device according to claim 1, wherein the linear oscillating actuating movement of the actuating component is an axial actuating movement.

3. The device according to claim 1, wherein the actuating component and the counter component are arranged in a kinematic chain.

4. The device according to claim 1, wherein the mass of the actuating component is essentially equal to the mass of the counter component.

5. The device according to claim 1, wherein a spring element is assigned to the actuating component during the linear oscillating actuating movement of the actuating component at least in terms of a forward movement or at least in terms of a backwards movement.

6. The device according to claim 1, wherein a spring element is assigned to the counter component during the linear oscillating actuating movement of the actuating component at least in terms of a forward movement or at least in terms of a backwards movement.

7. The device according to claim 1, wherein the counter component is designed as a passive component, which is passively moved during the linear oscillating actuating movement of the actuating component.

8. The device according to claim 1, wherein the counter component is designed as an active component.

9. The device according to claim 1, wherein the actuating device is configured to actuate the actuating component and/or the counter component in a mechanically contact-free manner.

10. The device according to claim 1, further comprising a plurality of chain elements connecting the actuating component and the counter component in an articulated manner.

11. The device according to claim 10, wherein the actuating device is configured to actuate the actuating component and/or the counter component in a mechanically contact-free manner.

12. The device according to claim 1, wherein the mechanical coupling of the actuating component and the piercing unit is along an axis of movement of the oscillating force produced by the vibration drive.

13. An actuation module for a device for piercing an organic tissue, comprising:
a module housing;
an actuating device arranged within the module housing and having an actuating component and a counter component assigned to the actuating component, the actuating component being mechanically coupled to a piercing unit;
a vibration drive selected from the following group: a parallel vibration motor, a Lorentz force-driven linear actuator with movable coil or movable rotors, a Piezo actuator, an ultrasonic actuator, a pneumatic vibration actuator and an electrodynamic linear actuator,
wherein the actuating device is driven directly by the vibration drive to produce a linear oscillating actuating movement of at least the actuating component free of any conversion of a rotary drive movement;
wherein the counter component is connected so as to move in a linear oscillating manner in the module housing and contrary to the direction of the actuating component during any oscillating actuating movement of the driven actuating device so as to at least partially compensate for the vibrations in the module housing that are caused by any oscillating actuating movement of the actuating component.

14. The actuation module according to claim 13, further comprising a plurality of chain elements connecting the actuating component and the counter component in an articulated manner.

15. The actuation module according to claim 14, wherein the mass of the actuating component is essentially equal to the mass of the counter component.

16. The actuation module according to claim 15, wherein the counter component is designed as a passive component which is passively moved during the linear oscillating actuating movement of the actuating component.

17. The actuation module according to claim 15, wherein the counter component is designed as an active component.

18. The actuation module according to claim 14, wherein the actuating device is configured to actuate the actuating component and/or the counter component in a mechanically contact-free manner.

* * * * *